(12) United States Patent
Adjei et al.

(10) Patent No.: US 7,056,494 B2
(45) Date of Patent: *Jun. 6, 2006

(54) METHOD OF TREATING A SYSTEMIC DISEASE

(75) Inventors: Akwete L. Adjei, Bridgewater, NJ (US); Perry Genova, Chapel Hill, NC (US); Yazping Zhu, Highland Park, NJ (US); Federick Sexton, Fair Haven, NJ (US)

(73) Assignee: Kos Pharmaceuticals, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/391,053

(22) Filed: Mar. 18, 2003

(65) Prior Publication Data

US 2004/0042967 A1    Mar. 4, 2004

Related U.S. Application Data

(63) Continuation of application No. 10/234,824, filed on Sep. 3, 2002, now abandoned.

(51) Int. Cl.
*A61K 9/12* (2006.01)
*A61M 11/00* (2006.01)

(52) U.S. Cl. .................. 424/45; 514/2; 128/200.14; 128/204.23; 128/200.24

(58) Field of Classification Search .................. 424/45, 424/46, 489; 128/200.14, 200.22, 204.18, 128/204.23, 200.24; 514/2
See application file for complete search history.

(56) References Cited

U.S. PATENT DOCUMENTS 5,743,252 A * 4/1998 Rubsamen et al. .... 128/200.14
5,819,726 A * 10/1998 Rubsamen et al. .... 128/200.14
6,406,681 B1 * 6/2002 Adjei et al. .................... 424/45

* cited by examiner

Primary Examiner—Sreeni Padmanabhan
Assistant Examiner—Mina Haghighatian

(57) ABSTRACT

A method and dispenser for treating a systemic disease in a patient in need of such treatment is disclosed. The method comprising maintaining the inspiratory flow rate and volume of the patient to a certain value and then administering a medicament aerosol formulation to the patient using a breath activated inhalation device.

**7 Claims, 1

METHOD OF TREATING A SYSTEMIC DISEASE

This application is a continuation of application Ser. No. 10/234,824 filed on Sep. 3, 2002, now abandoned, which is incorporated by reference hereinto in its entirety.

This application makes reference to U.S. Pat. No. 6,136, 294 and U.S. Pat. No. 6,261,539, which are incorporated hereinto by reference in their entirety.

BACKGROUND OF THE INVENTION

1. Field of the Invention

This invention relates to a method of treating a systemic disease, and more particularly, to a method which involves administering to a patient a medicinal aerosol spray from a pressurized metered dose inhaler using a breath activated inhaler device, taking into consideration the inspiratory flow rate and inspiratory volume of the patient, dosing time, dosing period and duration of the administration.

2. Description of the Related Art

The treatment of a systemic disease with a medicament aerosol regimen is a standard practice. However, the practice employed is typically hit and miss in terms of a dosage regimen which is one which is maximized in its effect. What is needed and desired is a device and method of treating a systemic disease, e.g. diabetes, immune deficiency, pain, etc., taking into consideration the critical parameters of application.

Heretofore while the treatment of systemic diseases may utilize an aerosol medium, it has been typically by way of manual devices. For example manual activated inhaler devices have been utilized. In this regard use of these manually actuated devices requires that the spray be activated at the beginning of the inspiratory cycle, so that the medication is carried into the lungs rather than being deposited in the mouth or throat. If this actuation is not correctly coordinated with the inspiratory phase, the metered dose may be deposited differently with each actuation and potentially compromise the therapeutics and safety of the product. A breath actuated device helps eliminate this problem by making the product easier to coordinate and more patient friendly with predictable delivery and dispersion in the respiratory airways including deep within the lungs.

There are numerous factors leading to poor coordination of actuation of the spray and the inspiration cycle. Including in those factors are the inherent limitations of the users, such as impaired physical abilities associated with geriatric patients or the as-yet-undeveloped skills of children, or the inability of either group to comprehend the correct way to use the device. Recognizing the need for correct and accurately delivered doses, particularly in patients with respiratory illnesses, a reliable breath activated device would improve the quality of life for these afflicted people.

SUMMARY OF THE INVENTION

This invention relates to a method of treating a systemic disease in a patient, and more particularly, treating such disease with a medicinal aerosol using pressurized Metered Dose Inhaler ("pMDI") and more particularly a breath activated inhaler ("BAI") device.

DETAILED DESCRIPTION OF THE INVENTION

Figure 1:
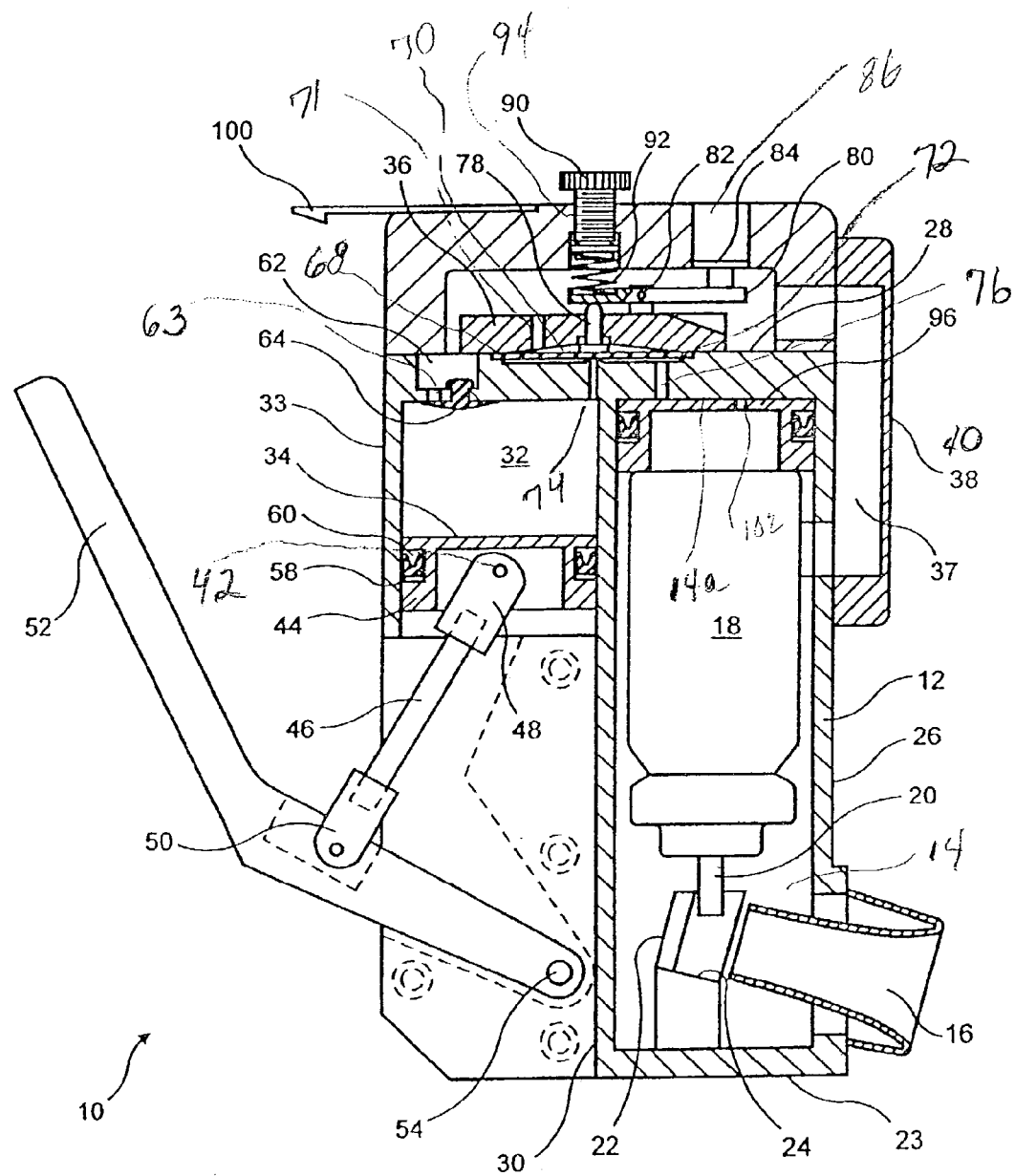
FIG. 1 is a side sectional view of a breath activated inhaler of the type shown in U.S. Pat. No. 6,328,035 B1.

This invention involves a method of treating a systemic disease, e.g. diabetes, and other hormone dependent maladies, immune deficiency, cancer, infection, pain, etc., in a patient, e.g. a human being or another animal, with a medicament or drug aerosol which comprises employing a breath activation device containing (a) the selected medicament, (b) a suitable fluid or propellant and having (a') a dose metering device and (b') a dose timing element. A suitable medicament includes therapeutic categories of drugs or medicaments such as cardiovascular drugs, antiallergics, antihistamines, antitussives, antifungals, antivirals, antibiotics, pain medicaments, antiinflammatories, steroids; biotherapeutics, including peptides, proteins, oligonucleotides, and gene vectors.

A suitable breath activated inhalation device is selected. A suitable device can be of any conventional design which has or is capable of being adapted to have, using any conventional means, such as mechanics, electromechanics, pneumatics, fluid dynamics, a trigger force of about 0.1 to about 20 cm of water pressure. By "trigger force" is meant a force means that is minimally required by the patient to activate the dosing mechanism associated with the device.

A typical pharmaceutical "pMDI" is a pressurized dosage form inhaler designed to deliver therapeutic agents, e.g. medicaments, to the human respiratory tract. Accordingly, the MDI contains the active substance, dissolved or suspended, in a fluid propellant system which contains at least one liquefied gas in a pressurized container that is sealed with a metering valve. The actuation of the valve delivers a metered dose of medicament in the form of an aerosol spray which is directed by a suitable adapter/activator for administration via oral or nasal inhalation.

Breath activated devices specifically for use with a pressurized metered dose inhaler system are comprised primarily of an inhalation sensing means and a means to actuate the canister automatically upon an appropriate inhalation profile. These devices may, therefore, generally be categorized by inhalation sensing means and canister activation means.

Inhalation may be sensed by measuring changes in pressure through the device or by measuring flow rate, directly or indirectly and separately or in combination. The literature is replete with methods for accomplishing this and includes moving vanes or flaps, elastomeric diaphragms, electronic pressure sensors, flow sensors, and combinations of mechanical sensors with electronic timing circuits. Examples of breath activated inhalation devices employing mechanical sensing using flaps, vanes or diaphragms are described in U.S. Pat. Nos. 6,328,035; 5,826,571; 5,507,281; 5,447,150; 5,217,004; 5,119,806; 5,069,204; 5,060,643; 4,803,978; 4,664,107; 3,826,413; 3,814,297; 3,636,949; 3,598,294; 3,565,070; 3,456,646; 3,456,645; 3,456,644; 3,356,088; 3,157,179; and 3,187,748. Examples of BAI devices employing electronic sensing are described in U.S. Pat. Nos. 5,826,570; 5,819,726; 5,692,492; 5,655,516; 5,404,871 and 4,648,393.

The canister may be actuated by mechanical (e.g. springs, levers, etc.) electromechanical (e.g. solenoids, motors) or pneumatic means. The canister may be actuated and remain in the actuated position until intervened upon by the patient or may be caused to dwell in the actuated position for some duration returning automatically to rest position without any intervention. Examples employing mechanical actuation are described in U.S. Pat. Nos. 5,826,571; 5,447,150; 5,217,004; 5,119,806; 5,069,204; 5,060,643; 5,027,808; 4,955, 371; 4,083,978; 4,664,107; 3,826,413; 3,814,297; 3,636,949; 3,598,294; 3,565,070; 3,456,646; 3,456,645; 3,456,644; 3,356,088; 3,157,179; and 3,187,748. Examples employing electromechanical actuation are described in U.S. Pat. Nos. 5,692,492; and 5,347,998. An example employing pneumatic actuation is described in U.S. Pat. No. 6,328,035. Examples of BAI devices which provide means for the canister returning automatically from the fired position are described in U.S. Pat. Nos. 5,826,571; 5,217,004; 5,119,806; 5,027,808; and 6,328,035.

All of the above-noted U.S. patents are incorporated hereinto by reference in their entirety.

Referring now to FIG. 1, there is illustrated a pMDI, breath activated inhaler 10, While this device is described in detail in U.S. Pat. No. 6,328,035 B1, which is incorporated by reference hereinto in its entirety, some brief comments are in order. It should be noted however that while this particular BAI is shown and described, it is merely illustrative of a BAI since any suitable metered dose BAI may be utilized to practice the invention herein described.

The breath activated inhaler device 10, comprises a housing 12 having a chamber 14 opening at mouthpiece 16. Aerosol canister 18 is mounted within the chamber 14, with the canister valve stem 20 pointed downwardly and located inside nozzle 22 and positioned just above the impinging surface 24. This surface is shown as a relatively flat surface. When the valve stem is impinged against it, in response to displacement of the canister during the pneumatic actuation, the medicine is discharged as an aerosol. The nozzle 22 directs the spray outward into the mouthpiece 16.

The first chamber 14 is defined by lower wall 23, outer wall 26, both of the housing 12, mouth piece 16, upper surface 28 and partitioning wall 30. A second chamber 32 is formed on the other side of partitioning wall 30, defined by the partitioning wall 30, upper surface 28, and outer wall 33. A movable piston 34 provides the lower surface of the second chamber 32. The second chamber is variable with respect to the location of the piston 34 within the chamber, and in fact the piston is used to compress an initial volume of gas into a smaller one, which increases the pressure of the gas. The energy stored in the compressed gas is used to effect the discharge of the medicine from the canister. There is a third chamber 37 of the device, defined by the outer wall 12, upper surface 28, transfer valve cover 36 and airway cover 40.

The upper portion of the compression piston 34 is attached to piston support 42 forming compression piston assembly 44. Connecting link 46 is affixed to the compression piston assembly at first end 48. The second end 50 of the connecting link 46 is affixed to the cocking lever 52. The cocking lever 52 is pivotally mounted about axial attachment rod 54, which fixedly attaches the cocking lever 52 to the housing. The cocking lever pivots between an charging position and a firing position.

The compression piston 34 is a cylinder that is dimensioned to fit snugly against the inner walls of the second chamber 32 and is formed of a solid, non impervious material, so that when the piston is moved into the cocked position, the fluid within the second chamber is compressed. The piston is provided with U-cup seals 58 which are situated within openings 60 in the piston assembly 44. In the place of the piston seals, such a rolling diaphragm seal, or a bellows-type system can also be used. The connecting link 46 could also be replaced by several links configured to toggle, negating the need for a latch.

The upper surface 28 in the second chamber 32 has an aperture 62 into which an elastomeric umbrella check valve 64 is fitted. When the pump lever is moved away from the body of the device, the connecting link 46 pulls the compression piston 34 downward. This action draws ambient air past the umbrella check valve 64 through passage 63 and into the second chamber 32.

A transfer valve cover 36 is located upon the upper surface 28 which defines the first and second cavities 14 and 32. The transfer valve 36 cover contains an elastomeric diaphragm 68 that is provided in a fluid pathway 70 between the transfer valve cover 36 and the upper surface 28 of the housing. The elastomeric diaphragm 68 is clamped at its periphery between the transfer valve cover 36 and the upper surface 28 of the housing to form an airtight seal. There is a shallow chamber 72 beneath the diaphragm with an orifice 74. When the pathway 70 is open, the pathway 70 and second chamber 32 are in fluid communication with each other. Also provided is a transfer port 76, which is an orifice that is in fluid communication with a chamber 14a which is a subchamber of chamber 14 and is positioned between surface 28 and actuation piston 96 and is formed by the movement thereof. When the pathway 70 is open, the pathway 70 and chamber 14a are in fluid communication with each other, and the compressed fluid can flow from the second chamber to the chamber 14a.

Above the diaphragm 68 there is a pin 78 that passes through the transfer valve cover 36 and presses against the diaphragm 68, providing a counterforce against the compressed fluid in the second chamber 32, insuring that the diaphragm is sealed. At its top, the pin 78 is maintained in place by the airway door support 80, mounted about pivot 82. At its right hand end, the airway door support 80 provided with airway door 84, shown as resembling a nail and its head, wherein the head is dimensioned to fit into and seal an aperture 86. On its left-hand side, airway door support 80 is provided with a groove or receptacle 94 for receiving biasing spring 92. Above the receptacle 94, airway frame 40 is provided with a threaded aperture 88 into which an adjustable screw 90 is fitted. The biasing spring 92 is connected to the adjustable screw 90 at one end and at the other end is positioned in the groove or receptacle 94 on the airway door support 80. Screw 90 provides for a tensioning of the spring 92 to a desired level. Of course, the screw 90 can be eliminated, with an appropriately pretensioned spring utilized, thereby substituting for the screw 90, spring 92 combination. Other means suitable for purpose may also be utilized in this regard.

The tension provided by the spring causes the airway door to press downwardly on the diaphragm 68, thereby effecting a seal which will maintain the pressurized fluid in the second chamber until the device is actuated.

The transfer valve cover 36 contains the charge of compressed air in the second chamber 32 until the user inhales from the device. When sufficient vacuum is created in the device, the transfer valve snaps open and allows pressure to transfer from the second chamber 32, to the first chamber 14a.

After a canister has been loaded into the first chamber, the user moves the cocking lever 52 away from the device and then moves it inwards towards the housing. When the cocking lever is moved away from the body of the device, the connecting link 46 pulls the compression piston 34 downward. This action draws ambient air past the umbrella check valve 64 through passage 63 and into the compression cylinder. The cocking lever 52 is then moved back to its original position adjacent to the body of the device, forcing the compression piston upward, thereby reducing the volume in the chamber and compressing the fluid in the chamber. A latch 100 provided in the airway frame 40 latches to the top end of the cocking lever 52 and restrains it while the piston is compressing the fluid.

When the user inhales through the mouthpiece 16, creating vacuum inside the device (specifically, in the first and third chambers 14 and 37, and in the upper space of the fluid pathway 70 through vent orifice 71), the differential pressure across the diaphragm 68 increases rapidly, instantaneously exceeding a threshold value at which the biasing spring 92 can no longer keep the diaphragm in the sealed position. The diaphragm 68 snaps open and the compressed fluid exits the second chamber 32, traverses the fluid pathway 70, and enters the first chamber 14 through transfer port 76, applying pressure to the actuation piston 96. The force acting on the actuation piston 96 overcomes the return spring in the canister valve 20, moving the canister and/or valve to cause the dispensation of the medicine as an aerosol. The medicine is dispensed through the nozzle 22 and mouthpiece 16. As the diaphragm 68 snaps open, the airway door 84, contemporaneously opens which allows the user to suck air therethrough while the medication is being dispensed. A bleed orifice 102 in the crown of the actuation piston 96 slowly bleeds off the compressed air contained between the upper surface 28 and the piston 96, permitting the canister return spring (not shown) to push the piston back to its original position after the dosing period, without user intervention. This prevents canister leakage that can occur if the valve stem remains depressed for prolonged periods. Moreover, as the pressure equalizes throughout the interior of the device, the biasing spring 92 returns the diaphragm 68 to the sealed position.

It should be evident to the skilled artisan that inhalation and discharge of the medicine from the container are very quick, which insures that the inhalation of the medicine commences at the beginning of the inhalation, insuring delivery of the drug to a greater degree of targeted surface area, which preferably is the lungs, than is usually possible.

For purposes of this application the following terms are defined as follows with regard to the formulation for the medication to be dispensed.

The terms "peptide", "polypeptide", "oligopeptide" and "protein" shall be used interchangeably when referring to peptide or protein drugs and shall not be limited as to any particular molecular weight, peptide sequence or length, field of bioactivity or therapeutic use unless specifically stated.

A suitable medicament to which the subject invention is directed includes a peptide, polypeptide, or protein biotherapeutic medicament ranging from 0.5 K Dalton to 250 K Dalton in molecular size. In particular, the peptide, polypeptide, or protein biotherapeutic medicament includes diabetic aids; such as insulins and insulin analogs; amylin; glucagon; surfactants; immunomodulating peptides such as cytokines, chemokines, lymphokines; interleukins, such as taxol, interleukin-1, interleukin-2, and interferons; erythropoetins; thrombolytics and heparins; anti-proteases, antitrypsins and amiloride; rhDNase; antibiotics and other antiinfectives; hormones; and growth factors, such as parathyroid hormones, LH-RH and GnRH analogs; nucleic acids; DDAVP; calcitonins; cyclosporine; ribavirin; enzymes; heparins; hematopoietic factors; cyclosporins; vaccines; immunoglobulins; vasoactive peptides; antisense agents; genes, oligonucleotide, and nucleotide analogs.

The term "diabetic aid" includes natural, synthetic, semi-synthetic and recombinant medicaments such as activin, glucagon, insulin, somatostatin, proinsulin, amylin, and the like.

The term "insulin" shall be interpreted to encompass insulin analogs, natural extracted human insulin, recombinantly produced human insulin, insulin extracted from bovine and/or porcine sources, recombinantly produced porcine and bovine insulin and mixtures of any of these insulin products. The term is intended to encompass the polypeptide normally used in the treatment of diabetics in a substantially purified form but encompasses the use of the term in its commercially available pharmaceutical form, which includes additional excipients. The insulin is preferably recombinantly produced and may be dehydrated (completely dried) or in solution.

The terms "insulin analog," "monomeric insulin" and the like are used interchangeably herein and are intended to encompass any form of "insulin" as defined above, wherein one or more of the amino acids within the polypeptide chain has been replaced with an alternative amino acid and/or wherein one or more of the amino acids has been deleted or wherein one or more additional amino acids has been added to the polypeptide chain or amino acid sequences, which act as insulin in decreasing blood glucose levels. In general, the term "insulin analogs" of the present invention include "insulin lispro analogs," as disclosed in U.S. Pat. No. 5,547,929, incorporated hereinto by reference in its entirety; insulin analogs including LysPro insulin and humalog insulin, and other "super insulin analogs", wherein the ability of the insulin analog to affect serum glucose levels is substantially enhanced as compared with conventional insulin as well as hepatoselective insulin analogs which are more active in the liver than in adipose tissue. Preferred analogs are monomeric insulin analogs, which are insulin-like compounds used for the same general purpose as insulin, such as insulin lispro, i.e., compounds which are administered to reduce blood glucose levels.

The term "amylin" includes natural human amylin, bovine, porcine, rat, rabbit amylin, as well as synthetic, semi-synthetic or recombinant amylin or amylin analogs including pramlintide and other amylin agonists, as disclosed in U.S. Pat. No. 5,686,411 and U.S. Pat. No. 5,854,215, both of which are incorporated hereinto by reference in their entirety.

The term "immunomodulating proteins" include cytokines, chemokines, lymphokines complement components, immune system accessory and adhesion molecules and their receptors of human or non-human animal specificity. Useful examples include GM-CSF, IL-2, IL-12, OX40, OX40L (gp34), lymphotactin, CD40, CD40L. Useful examples include interleukins, for example interleukins 1 to 15; interferons alpha, beta or gamma; tumor necrosis factor, granulocyte-macrophage colony stimulating factor (GM-CSF), macrophage colony stimulating factor (M-CSF), granulocyte colony stimulating factor (G-CSF), chemokines, such as neutrophil activating protein (NAP); macrophage chemoattractant and activating factor (MCAF), RANTES, macrophage inflammatory peptides MIP-1a and MIP-1b, complement components and their receptors, or an accessory molecule, such as B7.1, B7.2, ICAM-1, 2 or 3 and cytokine receptors. OX40 and OX40-ligand (gp34) are further useful examples of immunomodulatory proteins. Immunomodulatory proteins can for various purposes be of human or non-human animal specificity and can be represented, for present purposes, as the case may be and as may be convenient, by extracellular domains and other fragments with the binding activity of the naturally occurring proteins, and muteins thereof, and their fusion proteins with other polypeptide sequences, e.g. with immunoglobulin heavy chain constant domains. Where nucleotide sequences encoding more than one immunomodulating protein are inserted, they can, for example, comprise more than one cytokine or a combination of cytokines and accessory/adhesion molecules.

The term "interferon" or "IFN" as used herein means the family of highly homologous species-specific proteins that inhibit viral replication and cellular proliferation and modulate immune response. Interferons are grouped into three classes based on their cellular, origin and antigenicity, namely, alpha-interferon (leukocytes), beta-interferon (fibroblasts) and gamma-interferon (immunocompetent cells). Recombinant forms and analogs of each group have been developed and are commercially available. Subtypes in each group are based on antigenic/structural characteristics. At least 24 interferon alphas (grouped into subtypes A through H) having distinct amino acid sequences have been identified by isolating and sequencing DNA encoding these peptides. Reference is made to Viscomi, 1996 Biotherapy 10:59–86, the contents of which are incorporated by reference hereinto in its entirety. The terms "alpha.-interferon", "alpha interferon", "interferon alpha", "human leukocyte interferon" and "IFN" are used interchangeably herein to describe members of this group. Both naturally occurring and recombinant alpha interferons, including consensus interferon such as that described in U.S. Pat. No. 4,897,471, the contents of which are incorporated hereinto by reference in its entirety, may be used in the practice of the invention. Human leukocyte interferon prepared in this manner contains a mixture of human leukocyte interferons having different amino acid sequences. Purified natural human alpha interferons and mixtures thereof which may be used in the practice of the invention include but are not limited to Sumiferon RTM interferon alpha-n1 available from Sumitomo, Japan; Welfferong interferon alpha-n1 (Ins) available from Glaxo-Wellcome Ltd., London, Great Britain; and Alferon RTM interferon alpha-n3 available from the Purdue Frederick Co., Norwalk, Conn.

The term "erythropoietin" applies to synthetic, semi-synthetic, recombinant, natural, human, monkey, or other animal or microbiological isolated polypeptide products having part or all of the primary structural conformation (i.e., continuous sequence of amino acid residues) and one or more of the biological properties (e.g., immunological properties and in vivo and in vitro biological activity) of naturally-occurring erythropoietin, including allelic variants thereof. These polypeptides are also uniquely characterized by being the product of procaryotic or eucaryotic host expression (e.g., by bacterial, yeast and mammalian cells in culture) of exogenous DNA sequences obtained by genomic or cDNA cloning or by gene synthesis. Products of microbial expression in vertebrate (e.g., mammalian and avian) eells may be further characterized by freedom from association with human proteins or other contaminants which may be associated with erythropoietin in its natural mammalian cellular environment or in extracellular fluids such as plasma or urine. The products of typical yeast (e.g., Saccaromyces cerevisiae) or procaryote (e.g., E. coli) host cells are free of association with any mammalian proteins. Depending upon the host employed, polypeptides of the invention may be glycosylated with mammalian or other eucaryotic carbohydrates or may be nonglycosylated. Polypeptides of the invention may also include an initial methionine amino acid residue (at position–1). Novel glycoprotein products of the invention include those having a primary structural conformation sufficiently duplicative of that of a naturally-occurring (e.g., human) erythropoietin to allow possession of one or more of the biological properties thereof and having an average carbohydrate composition which differs from that of naturally-occurring (e.g., human) erythropoietin.

The terms "heparins" and "thrombolytics" include anti-clotting factors such as heparin, low molecular weight heparin, tissue plasminogen activator (TPA), urokinase (Abbokinase) and other factors used to control clots.

The terms "anti-proteases" and "protease-inhibitors" are used interchangeably and apply to synthetic, semi-synthetic, recombinant, naturally-occurring or non-naturally occurring, soluble or immobilized agents reactive with receptors, or act as antibodies, enzymes or nucleic acids. These include receptors which modulate a humoral immune response, receptors which modulate a cellular immune response (e.g., T-cell receptors) and receptors which modulate a neurological response (e.g., glutamate receptor, glycine receptor, gamma-amino butyric acid (GABA) receptor). These include the cytokine receptors (implicated in arthritis, septic shock, transplant rejection, autoimmune disease and inflammatory diseases), the major histocompatibility (MHC) Class I and II receptors associated with presenting antigen to cytotoxic T-cell receptors and/or T-helper cell receptors (implicated in autoimmune diseases) and the thrombin receptor (implicated in coagulation, cardiovascular disease). Also included are antibodies which recognize self-antigens, such as those antibodies implicated in autoimmune disorders and antibodies which recognize viral (e.g., HIV, herpes simplex virus) and/or microbial antigens.

The terms "hormones" and "growth factors" include hormone releasing hormones such as growth hormone, thyroid hormone, thyroid releasing hormone (TRH), gonadotropin-releasing hormone (GnRH), leuteininzing hormone, leuteininzing hormone-releasing hormone (LHRH, including the superagonists and antagonists, such as leuprolide, deltirelix, gosorelin, nafarelin, danazol, etc.) sourced from natural, human, porcine, bovine, ovine, synthetic, semi-synthetic, or recombinant sources. These also include somatostatin analogs such as octreotide (Sandostatin). Other agents in this category of biotherapeutics include medicaments for uterine contraction (e.g., oxytocin), diuresis (e.g., vasopressin), neutropenia (e.g., GCSF), medicaments for respiratory disorders (e.g., superoxide dismutase), RDS (e.g., surfactants, optionally including apoproteins), and the like.

The term "enzymes" include recombinant deoxyribonuclease such as DNAse (Genentech) proteases (e.g., serine proteases such as trypsin and thrombin), polymerases (e.g., RNA polymerases, DNA polymerases), reverse transcriptases and kinases, enzymes implicated in arthritis, osteoporosis, inflammatory diseases, diabetes, allergies, organ transplant rejection, oncogene activation (e.g., dihydrofolate reductase), signal transduction, self-cycle regulation, transcription, DNA replication and repair.

The term "nucleic acids" includes any segment of DNA or RNA containing natural or non-naturally occurring nucleosides, or other proteinoid agents capable of specifically binding to other nucleic acids or oligonucleotides via complementary hydrogen-bonding and also are capable of binding to non-nucleic acid ligates. In this regard, reference is made to Bock, L., et al., Nature 355:564–566 (1992) which reports inhibition of the thrombin-catalyzed conversion of fibrinogen to fibrin using aptamer DNA.

Examples of biological molecules for which lead molecules can be synthesized and selected and combined in accordance with the invention include, but are not limited to, agonists and antagonists for cell membrane receptors, neurotransmitters, toxins and venoms, viral epitopes, hormones, opiates, steroids, peptides, enzyme substrates and inhibitors, cofactors, drugs, lectins, sugars, oligonucleotides, nucleic acids, oligosaccharides, lipids, proteins, and analogs of any of the foregoing molecules.

The term "analog" refers to a molecule, which shares a common functional activity with the molecule to which it is deemed to be comparable and typically shares common structural features as well.

The term "recombinant" refers to any type of cloned biotherapeutic expressed in procaryotic cells or a genetically engineered molecule, or combinatorial library of molecules which may be further processed into another state to form a second combinatorial library, especially molecules that contain protecting groups which enhance the physicochemical, pharmacological, and clinical safety of the biotherapeutic agent.

The term "vaccines" refers to therapeutic compositions for stimulating humoral and cellular immune responses, either isolated, or through an antigen presenting cell, such as an activated dendritic cell, that is able to activate T-cells to produce a multivalent cellular immune response against a selected antigen. The potent antigen presenting cell is stimulated by exposing the cell in vitro to a polypeptide complex. The polypeptide complex may comprise a dendritic cell-binding protein and a polypeptide antigen, but preferably, the polypeptide antigen is either a tissue-specific tumor antigen or an oncogene gene product. However, it is appreciated that other antigens, such as viral antigens can be used in such combination to produce immunostimulatory responses. Preferably, the dendritic cell-binding protein that forms part of the immunostimulatory polypeptide complex is GM-CSF. More preferably, the polypeptide antigen that forms part of the complex is the tumor-specific antigen prostatic acid phosphatase. Yet also preferably, the polypeptide antigen may be any one of the oncogene product peptide antigens. The polypeptide complex may also contain, between the dendritic cell-binding protein and the polypeptide antigen, a linker peptide. The polypeptide complex may comprise a dendritic cell-binding protein covalently linked to a polypeptide antigen, such polypeptide complex being preferably formed from a dendritic cell binding protein, preferably GM-CSF, and a polypeptide antigen. The polypeptide antigen is preferably a tissue-specific tumor antigen such as prostatic acid phosphatase (PAP), or an oncogene product, such as Her2, p21RAS, and p53; however, other embodiments, such as viral antigens, are also within the scope of the invention.

The term "immunoglobulins" encompasses polypeptide oligonucleotides involved in host defense mechanisms, such as coding and encoding by one or more gene vectors, conjugating various binding moieties of nucleic acids in host defense cells, or coupling expressed vectors to aid in the treatment of a human or animal subject. The medicaments included in this class of polypeptides include IgG, IgE, IgM, IgD, either individually or in a combination with one another.

The selected medicament is preferably in particulate form for treatment of systemic disease via aerosol delivery by way of the pMDI having the breath activated feature. Accordingly, the drug or medicament should have a diameter ranging from about 1 to about 7 micrometers.

The biotherapeutic medicament is present in the formulations in a therapeutically effective amount, that is, an amount such that the biotherapeutic medicament can be incorporated into an aerosol formulation such as a dispersion, aerosol, via oral inhalation or nasal inhalation, and cause its desired therapeutic effect, typically preferred with one dose, or through several doses. The drug is typically administered as an aerosol from a conventional valve, e.g. a metered dose valve, through an aerosol adapter also known as an actuator.

For purposes of this application the following terms are defined as follows with regard to the BAI and the medication to be dispensed.

The term "dosing interval" shall be interpreted to mean the period during which administration of the selected medicament may be given to a patient in need thereof by the intrapulmonary route of administration which period may encompass preferably from about every 1 to about 10 hours in a day for a suitable dosing time of about 200 to about 2000 milliseconds during the patient's inspiratory cycle.

The term "inspiratory cycle" is used herein to refer to the total time used by a patient to breath in air until just before exhalation commences, i.e., the time taken to ventilate a person's lungs completely.

The term "dosing timing element" as used herein shall be interpreted to mean a timer, a dose counter, time measuring device, or a time indicator which when incorporated into the aerosol device enables dose tracking, compliance monitoring, and/or dose triggering to a patient during administration of the aerosol medicament.

The term "dosing time" as used herein shall be interpreted to mean the timing in a patient's inspiratory cycle during which a single spray of formulation may be released to the patient via the intrapulmonary route of administration which event may commence at about 50 milliseconds to 2000 milliseconds into the inspiratory cycle of the said patient, which time may also conclude before exhalation commences.

The term "dosing period" as used herein shall be interpreted to encompass one or more releases of aerosolized medication over a period of time as required by the medicament's pharmacologic action.

The term "amount" as used herein refers to a quantity or to a concentration as appropriate to the context. The amount of a drug that constitutes a therapeutically effective amount varies according to factors such as the potency of the particular biotherapeutic medicament, the route of administration of the formulation, and the mechanical system used to administer the formulation. A therapeutically effective amount of a particular drug can be selected by those of ordinary skill in the art with due consideration of such factors. Preferably a suitable therapeutically effective amount of biotherapeutic medicament will be from about 0.00001 parts by weight to about 5 parts by weight based on 100 parts by weight of the fluid or propellant carrier selected.

A suitable fluid carrier is one that carries and transports the particles having a selected medicament and includes air, a hydrocarbon, such as n-butane, propane, isopentane, etc. or a propellant. A suitable propellant is any fluorocarbon, e.g. a 1–6 hydrogen containing flurocarbon (such as $CHF_2CHF_2$, $CF_3CH_2F$, $CH_2F_2CH_3$ and $CF_3CHFCF_3$), a perfluorocarbon, e.g. a 1–4 carbon perfluorocarbon, (such as $CF_3CF_3$, $CF_3CF_2CF_3$); or any mixture of the foregoing, having a sufficient vapor pressure to render them effective as propellants. Some typical suitable propellants include conventional chlorofluorocarbon (CFC) propellants such as propellants 11, 12 and 114 or a mixture thereof. Non-CFC propellants such as HFA propellants, such as 1,1,1,2-tetrafluoroethane (Propellant 134a), 1,1,1,2,3,3,3-heptafluoropropane (Propellant 227) or a mixture thereof are preferred. The fluid or propellant is preferably present in an amount sufficient to propel a plurality of selected doses of drug in the form of particles from an aerosol canister when such is employed.

Optionally, a suitable stabilizer is selected. A suitable stabilizer includes (1) an amino acid selected from (a) a monoamino carboxylic acid of the formula, $H_2N$—R—COOH (I), (b) a monoamino dicarboxylic acid of the formula, $H_2N$—$R(COOH)_2$ (II) and (c) a diamino monocarboxylic acid of the formula $(H_2N)_2$—R COOH (III), where R is a straight or branched alkyl radical of from 1 to 22 carbon atoms, which can be mono or poly-substituted with moieties such as sulfide (—S—), oxide (—O—), hydroxyl (—OH), amide (—NH), sulfate (—SO4); aryl of the formula $$\text{(benzene ring)}-X,$$

where X is hydrogen, halogen (F, Cl, BR, I), alkyl of 1 to 6 carbon atoms, alkoxy of 1 to 6 carbon atoms, hydroxy and nitro; and heterocyclic, such as thienyl, furyl, pyranyl, imidazolyl, pyrrolyl, thizolyl, oxazolyl, pyridyl, and pyrimidinyl compounds; (2) a derivative of the amino acid selected from (a) acid addition salts of the amino group, obtained from inorganic acids, such as hydrochloric, hydrobromic, sulfuric, nitric, phosphoric, and perchloric acids, as well as organic acids, such as tartaric, citric, acetic, succinic, maleic, fumaric, oxalic acids; (b) amides of the carboxylic acid group, e.g., glutamine, di-peptides, e.g. salts and esters of oxidized and unoxidized L-cysteinylglycine, gamma-L-glutamyl-L-cysteine, N-acetyl-L-cysteine-glycine, either conjugated, unconjugated or polymeric forms of L-Gly-L-Glu and L-Val-L-Thr, L-aspartyl-L-phenylalanine, muramyl dipeptides, nutrients such as L-tyrosyl-L-tyrosine, L-alanyl-L-tyrosine, L-arginyl-L-tyrosine, L-tyrosyl-L-arginine, N-Cbz-L-Leu-L-Leu-OCH and its salts or esters, glycylglycine, N-acetyl-L-aspartate-L-glutamate (NAAG), etc.; and tripeptides, e.g. oxidized and unoxidized gamma-L-glutamyl-L-cysteinylglycine; muramyl tripeptides, etc.; (c) esters of the carboxylic acid group obtained from aliphatic straight or branched chain alcohols of from 1 to 6 carbon atoms, e.g. L-aspaityl-L-phenylalanine methylester (Aspartame®), (3) an ether of any of the foregoing; (4) a hydrate or semi-hydrate of any of the foregoing and (5) a mixture of the amino acid and the derivative of the amino acid.

Suitable amino acids include glycine, alanine, valine, leucine, isoleucine, leucylalanine, methionine, threonine, isovaline, phenylalanine, tyrosine, serine, cysteine, N-acetyl-L-cysteine, histidine, tryptophan, proline, and hydroxyproline, e.g. trans-4-hydroxy proline. Compounds of the formula (II) include aspartic acid, and glutamic acid, compounds of the formula (III) include arginine, glutamine, lysine, hydroxylysine, ornithine, asparagine, and citrulline.

A fluid or aerosol formulation preferably comprises the protective colloid stabilizer in an amount effective to stabilize the formulation relative to an identical formulation not containing the stabilizer, such that the drug does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

For optimal functional and therapeutic performance of the aerosol formulation as an aerosol suspension, the stabilizer is present either as a coarse carrier (e.g., 20–90 μm) or as a finely micronized powder, $\leq 10$ μm in diameter. In either case, reproducible drug dosimetry is obtained without the need to qualify the inspiratory maneuver of the patient. Accordingly, excellent dose uniformity is obtained at tidal flows of up to 2 liters, or at inspiratory flow rates of as low as 15 liters per minute to about 90 liters per minute.

Alternatively, optionally, a second suitable stabilizer is selected instead of the first stabilizer. A second suitable stabilizer is a "water addition". As used herein a "water addition" is an amount of water which (1) is added, either initially with other components of the described aerosol formulation, e.g. medicament associated with the polymeric construct as part thereof or encapsulated therein, and fluid carrier, or after the other components, e.g. medicament, fluid carrier, are combined and processed, (2) is in addition to the water which is always present and which develops during processing and/or storage of the aerosol formulation, i.e. "developed" or "nascent" formulation water, and (3) is present in an amount which further stabilizes a medicinal aerosol formulation, e.g. rosiglitazone maleate, having nascent formulation water.

An aerosol formulation preferably comprises the water addition in an amount sufficient to more effectively stabilize the formulation relative to an identical formulation not containing the water addition, i.e. containing only nascent formulation water, such that the drug e.g., an insulin containing construct, does not settle, cream or flocculate after agitation so quickly as to prevent reproducible dosing of the drug. Reproducible dosing can be achieved if the formulation retains a substantially uniform drug concentration for about fifteen seconds to about five minutes after agitation.

The particular amount of stabilizer that constitutes an effective amount is dependent upon the particular stabilizer, the particular propellant, and on the particular drug used in the formulation. It is therefore not practical to enumerate specific effective amounts for use with specific formulations of the invention, but such amounts can readily be determined by those skilled in the art with due consideration of the factors set forth above. Generally, however, the stabilizer can be present in a formulation in an amount from about 0.001 parts per million to about 200,000 parts per million, more preferably about 1 part per million to about 10,000 parts per million, most preferably from about 10 parts per million to about 5,000 parts per million of the total formulation.

It has been found that the aforesaid formulation is stable without the necessity of employing a cosolvent, such as ethanol, or surfactants. However, further components, such as conventional lubricants or surfactants, co-solvents, ethanol, etc., can also be present in an aerosol formulation in suitable amounts readily determined by those skilled in the art. In this regard, reference is made to U.S. Pat. No. 5,225,183, which is incorporated by reference hereinto in its entirety.

Generally the aforesaid formulations can be prepared by combining (i) the biotherapeutic medicament or drug in an amount sufficient to provide a plurality of therapeutically effective doses of the biotherapeutic; (ii) if necessary, adding an appropriate suspension stabilizer in an amount effective to stabilize each of the formulations; (iii) dispersing the stabilized biotherapeutic medicament in an appropriate fluid or propellant in an amount sufficient to propel a plurality of doses, e.g. from an aerosol canister; and (iv) adding any further optional components, e.g. ethanol as a cosolvent; and homogenizing the components until a uniform dispersion is achieved. The components can be dispersed using a conventional mixer or homogenizer, by shaking, or by ultrasonic energy, such as disclosed in U.S. Pat. No. 6,116,234 incorporated by reference hereinto in its entirety. The components can also be dispersed using a bead mill or a microfluidizer. Bulk formulations can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. It has been found, however, that selection of appropriate valve assemblies for use with aerosol formulations is dependent upon the particular stabilizer and other adjuvants used (if any), on the propellant, and on the particular drug being used. Conventional neoprene and buna valve rubbers used in metered dose valves for delivering conventional CFC formulations often have less than optimal valve delivery characteristics and ease of operation when used with formulations containing HFC-134a or HFC-227. Therefore certain formulations are preferably dispensed via a valve assembly wherein the diaphragm is made of a nitrile rubber such as DB-218 (American Gasket and Rubber, Schiller Park, Ill.) or an EPDM rubber such as Vistalon™ (Exxon), Royalene™ (UniRoyal), bunaEP (Bayer). Also suitable are diaphragms fashioned by extrusion, injection molding or compression molding from a thermoplastic elastomeric material such as FLEXOMIER™ GERS 1085 NT polyolefin (Union Carbide).

Conventional aerosol canisters, coated or uncoated, anodized or unanodized, e.g., those of aluminum, glass, stainless steel, polyethylene terephthalate, and coated canisters or cans with epon, epoxy, etc., can be used to contain a formulation. The contents of the canister can be introduced into the canister by either the cold fill process or the pressure fill process. These processes as well as other processes, devices, etc., are described in "Metered Dose Inhaler Technology," Tol. S. Purewal et al., Ed., Interpharm Press Inc., 1998, which is incorporated by reference hereinto in its entirety.

The formulation may be administered via the intrapulmonary or intranasal route. The formulation of the invention can be delivered to the respiratory tract and/or lung of the patient to be treated, e.g. a human being or other animal, by oral inhalation. The formulation can also be delivered to the lung in order for the biotherapeutic agent to be delivered at measured rates to the systemic circulation for treatment of diseases elsewhere in the body, e.g., diabetes, hormone replacement, cancer, erythropoiesis, infection, or for immune protection such as achievable with vaccines. The formulations can also be delivered by nasal inhalation in order to treat, for example, allergic rhinitis, rhinitis, (local) or diabetes (systemic), or they can be delivered via topical (e.g., buccal) administration in order to treat, e.g., angina or local infection.

The formulations are used to treat systemic disease in a patient e.g. human being or another animal, suffering from such diseases. Initially, the inspiratory flow rate of the patient is established and maintained at a range of from 0.05 to about 2.0 liters per second. This is accomplished by allowing drug administration to be carried out under the patient's normal tidal flow. Additionally, each dose administered is timed to commence at about 50 milliseconds to about 2000 milliseconds during the inspiratory cycle.

Having established and maintained these parameters in the patient, the medicinal aerosol formulation comprising an effective amount, e.g. about 0.0001 parts to about 5 parts by weight to 100 parts by weight of the carrier, and the selected fluid carrier is administered to the patient at the suitable dosing time for the suitable dosing period, for about 1 to about 4 sprays of the aerosol formulation every 3 to 4 hours in a day in a dosing time of preferably about 50 to about 2000 milliseconds, e.g. about 200 to about 500 milliseconds.

In operation, the breath activated inhaler device having or being adapted to have a triggering device with a trigger force of about 0.01 to 20 cm, e.g. preferably 0.01 to 10 cm of the type noted in the aforenoted patents. Other breath activated inhaler devices suitable for the purpose may also be utilized. Typically, the device has a container, e.g., a pressure canister, for containing the selected medicament, e.g. insulin, and the selected propellant, e.g. air, CFC propellant, non-CFC or HFA propellant, which is destined to carry and transport the medicament as an aerosol, e.g., solution, suspension, powder.

A sensing means (see for example U.S. Pat. No. 6,328,035) is provided whereby when the patient to be treated inhales on the device and thereby has an inspiratory flow rate in the range of about 0.05 to about 2 liters per second, the sensing means triggers the triggering means. The triggering means then releases the propellant and medicament from the container and is directed to the patient's nose or mouth. Preferably the flow rate of the medication is low and is absorbed deep in the patient's lungs. The amount of medication dispensed and duration of dispensing will depend upon, among other things, the treatment being effected. The use of the pMDI and breath activated inhaler provides for easy and predictable delivery and dispersion in the respiratory air way particularly deep within the lungs.

We claim:

1. A method of treating a systemic disease via interpulmonary administration in a patient in need thereof, which consists essentially of:

(a) maintaining the inspiratory flow rate in the patient in a range of about 0.05 to about 2 liters per second and the inspiratory volume of the patient in the range of about 0.1 to about 5 liters; and (b) administering to the patient, using a pressurized breath activated metered dose device, a medicinal aerosol formulation comprising (a') a medicament suitable for systemic absorption via aerosol delivery present in an effective amount; and (b') a fluid propellant carrier for carrying and transporting said medicament at about 50 to about 2000 milliseconds for about 1 to about 4 sprays of the aerosol formulation about every 3 to 4 hours and (c') and a stabilizer selected from the group consisting of an amino acid, a derivative thereof, a water addition stabilizer and a mixture of any of the foregoing stabilizers.

2. The method as defined in claim 1 wherein said device has a triggering force of about 0.01 to about 20 cm of water.

3. The method as defined in claim 1 wherein said effective amount of medicament comprises from about 0.00001 parts by weight to about 10 parts by weight based on 100 parts by weight of said carrier.

4. The method as defined in claim 3 wherein said medicament is a solubilized or suspended particulate medicament having a diameter ranging from about 1 to about 7 micrometers.

5. The method as defined in claim 3 wherein said medicament comprises a protein or peptide medicament having a molecular size ranging from about 0.5 K Dalton to about 250 K Daltons.

6. A breath activated metered dose inhalation device for delivering to a person in need thereof a medicament in aerosol form for treating a systemic disease, which consists essentially of:
   (a) a container for controlling the medicament for treating systemic disease, a fluid propellant for carrying and transporting the medicament as an aerosol and a stabilizer selected from the group consisting of an amino acid, a derivative thereof, a water addition and a mixture of any of the foregoing stabilizers,
   (b) a triggering means such that when triggered by the inhalation of a patient releases said propellant and the medicament from said container; and
   (c) a sensing means for triggering said triggering means when the inspiratory flow rate in the patient is in the range of about 0.05 to about 2 liters per second and the inspiratory flow volume is in the range of about 0.1 to about 5 liters.

7. The device as defined in claim 6 which further includes a valve means for metering and dispensing the medicament and dispensing the medicament, said valve means comprising elements made from nitrile rubber, EPDM rubber, polyolefin or thermoplastic elastomeric material.

* * * * *